(12) United States Patent
Akioka

(10) Patent No.: US 10,385,021 B2
(45) Date of Patent: *Aug. 20, 2019

(54) CARBAMATE COMPOUND AND USE THEREOF

(71) Applicant: SUMITOMO CHEMICAL COMPANY, LIMITED, Chuo-ku, Tokyo (JP)

(72) Inventor: Yuki Akioka, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/541,799

(22) PCT Filed: Jan. 5, 2016

(86) PCT No.: PCT/JP2016/050072
§ 371 (c)(1),
(2) Date: Jul. 6, 2017

(87) PCT Pub. No.: WO2016/114161
PCT Pub. Date: Jul. 21, 2016

(65) Prior Publication Data
US 2017/0342032 A1  Nov. 30, 2017

(30) Foreign Application Priority Data

Jan. 13, 2015  (JP) ................. 2015-003941

(51) Int. Cl.
*C07D 213/30* (2006.01)
*A01N 47/20* (2006.01)
*A01N 43/40* (2006.01)

(52) U.S. Cl.
CPC ........... *C07D 213/30* (2013.01); *A01N 43/40* (2013.01); *A01N 47/20* (2013.01)

(58) Field of Classification Search
CPC ....... C07D 213/30; A01N 43/40; A01N 47/20
See application file for complete search history.

(56) References Cited

U.S. PATENT DOCUMENTS

| | | | |
|---|---|---|---|
| 5,538,940 A | 7/1996 | Sauter et al. | |
| 5,573,999 A | 11/1996 | Sauter et al. | |
| 5,824,705 A | 10/1998 | Mueller et al. | |
| 9,521,848 B2 | 12/2016 | Shioda et al. | |
| 2004/0157740 A1 | 8/2004 | Maurer et al. | |
| 2016/0150787 A1 | 6/2016 | Azuma et al. | |
| 2017/0105413 A1 | 4/2017 | Akioka et al. | |
| 2017/0105416 A1 | 4/2017 | Akioka et al. | |
| 2017/0360044 A1 | 12/2017 | Akioka | |
| 2018/0002294 A1 | 1/2018 | Akioka | |

FOREIGN PATENT DOCUMENTS

| | | |
|---|---|---|
| CN | 103910670 A | 7/2014 |
| EP | 0 335 519 A1 | 10/1989 |
| JP | 1-308206 A | 12/1989 |
| JP | 5-255191 A | 10/1993 |
| JP | 2004-531551 A | 10/2004 |
| WO | 93/15046 A1 | 8/1993 |
| WO | 2015/005499 | 3/2017 |

OTHER PUBLICATIONS

Patani et al. (Bioisosterism: A Rational Approach in Drug Design, 96 Chem. Rev., 1996, pp. 3147-3176).*
Gaikwad et al., (The Use of Bioisosterism in Drug Design and Molecular Modification, American Journal of PharmTech Research, 2012, 2(4), pp. 1-23).*
Singh et al. (International Journal of Pharma Sciences and Research, 2015, 6(5), pp. 939-947).*
Cambridge MedChem Consulting, 2012, (< https://www.cambridgemedchemconsulting.com/resources/bioisoteres/>, downloaded Sep. 5, 2018).*
Billingsley, K.L., et al. "Palladium-Catalyzed Borylation of Aryl Chlorides: Scope, Applications, and Computational Studies," Angewandte Chemie, International Edition, 46, 5359-5363 (2007).
European Patent Office, Extended European Search Report issued in corresponding Application No. EP 16737232, dated May 11, 2018.
European Patent Office, Extended European Search Report issued in corresponding Application No. EP 16737233, dated May 17, 2018.
European Patent Office, Extended European Search Report issued in corresponding Application No. EP 16737234, dated May 4, 2018.

(Continued)

*Primary Examiner* — Susanna Moore
(74) *Attorney, Agent, or Firm* — Stites & Harbison, PLLC; Terry L. Wright; Jeffrey A. Haeberlin

(57) ABSTRACT

A carbamate compound represented by formula (I), wherein,
$R^1$ represents a hydrogen atom or a C1-C3 alkyl group;
$R^2$, $R^3$, $R^4$ and $R^5$ each independently represents a hydrogen atom, a halogen atom, a C1-C3 alkyl group optionally having one or more halogen atoms, a C3-C4 cycloalkyl group optionally having one or more halogen atoms or a C1-C3 alkoxy group optionally having one or more halogen atoms;
$Z^1$ represents a C1-C3 alkyl group; and
m represents any one of integers from 1 to 4;
has an excellent effect of controlling plant diseases.

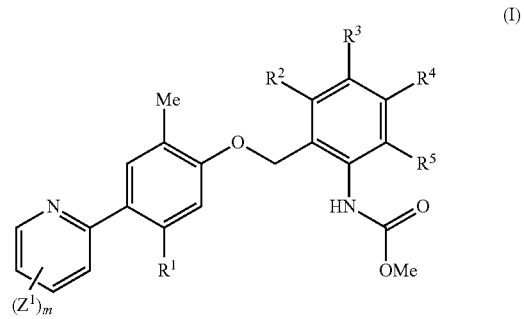

(I)

5 Claims, No Drawings

(56) References Cited

OTHER PUBLICATIONS

European Patent Office, Extended European Search Report issued in corresponding Application No. EP 16737235.8 (corresponds to U.S. Appl. No. 15/541,848, now U.S. Pat. No. 10,040,768) dated Aug. 30, 2018.
Intellectual Property India, Examination Report issued in corresponding Application No. 201737025884, dated Jun. 12, 2019.
Intellectual Property India, Examination Report issued in corresponding Application No. 201737025885 (equivalent to U.S. Appl. No. 15/541,821), dated May 31, 2019.
Intellectual Property India, Examination Report issued in corresponding Application No. 201737025887 (equivalent to U.S. Appl. No. 15/541,832, now U.S. Pat. No. 10,194,662), dated Apr. 23, 2019.
Intellectual Property India, Examination Report issued in corresponding Application No. 201737025888 (equivalent to U.S. Appl. No. 15/541,848, now U.S. Pat. No. 10,040,768), dated Apr. 23, 2019.

\* cited by examiner

CARBAMATE COMPOUND AND USE THEREOF

TECHNICAL FIELD

The present invention relates to carbamate compounds and use thereof.

BACKGROUND ART

For example, a compound represented by the following formula (X):

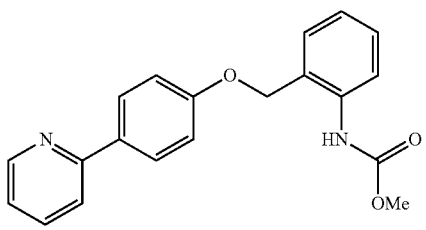

is known as an usable compound having a plant disease controlling effect (see U.S. Pat. No. 5,824,705).

CITATION LIST

Patent Literature

[PTL 1] U.S. Pat. No. 5,824,705

SUMMARY OF INVENTION

The present invention provides compounds having an excellent effect of controlling plant diseases.

According to the present invention, a carbamate compound represented by formula (I):

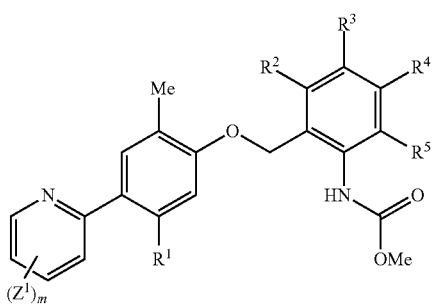

wherein,
$R^1$ represents a hydrogen atom or a C1-C3 alkyl group;
$R^2$, $R^3$, $R^4$ and $R^5$ each independently represents a hydrogen atom, a halogen atom, a C1-C3 alkyl group optionally having one or more halogen atoms, a C3-C4 cycloalkyl group optionally having one or more halogen atoms, or a C1-C3 alkoxy group optionally having one or more halogen atoms;
$Z^1$ represents a C1-C3 alkyl group; and
m represents any one of integers from 1 to 4, provided that when m is any integer from 2 to 4, two to four of $Z^1$ may be the same or different;
has an excellent plant disease controlling effect.

DESCRIPTION OF EMBODIMENT

In the expression of "optionally having one or more halogen atoms", in the case of two or more halogen atoms, the halogen atoms may be same or different.

In the present specification, the expressions of "C1-C3", "C3-C4" and "C1-C5" mean that the number of the carbon atoms is from 1 to 3, from 3 to 4, and from 1 to 5, respectively.

The halogen atom is a fluorine atom, a chlorine atom, a bromine atom or an iodine atom.

As the embodiment of the present carbamate compounds are exemplified the following compounds.

In the present invention, the carbamate compounds include:
a carbamate compound, wherein $R^1$ is a hydrogen atom or a methyl group;
a carbamate compound, wherein $R^1$ is a hydrogen atom;
a carbamate compound, wherein $R^1$ is a methyl group;
a carbamate compound, wherein $R^2$, $R^3$, $R^4$ and $R^5$ are hydrogen atoms;
a carbamate compound, wherein $R^2$ is a halogen atom, a C1-C3 alkyl group optionally having one or more halogen atoms, a C3-C4 cycloalkyl group optionally having one or more halogen atoms or a C1-C3 alkoxy group optionally having one or more halogen atoms, and $R^3$, $R^4$ and $R^5$ are hydrogen atoms;
a carbamate compound, wherein $R^2$ is a halogen atom, and $R^3$, $R^4$ and $R^5$ are hydrogen atoms;
a carbamate compound, wherein $R^2$ is a C1-C3 alkyl group optionally having one or more halogen atoms, and $R^3$, $R^4$ and $R^5$ are hydrogen atoms;
a carbamate compound, wherein $R^2$ is a C3-C4 cycloalkyl group optionally having one or more halogen atoms, and $R^3$, $R^4$ and $R^5$ are hydrogen atoms;
a carbamate compound, wherein $R^2$ is a C1-C3 alkoxy group optionally having one or more halogen atoms, and $R^3$, $R^4$ and $R^5$ are hydrogen atoms;
a carbamate compound, wherein $R^5$ is a halogen atom, a C1-C3 alkyl group optionally having one or more halogen atoms, a C3-C4 cycloalkyl group optionally having one or more halogen atoms or a C1-C3 alkoxy group optionally having one or more halogen atoms, and $R^2$, $R^3$ and $R^4$ are hydrogen atoms;
a carbamate compound, wherein $R^5$ is a halogen atom, and $R^2$, $R^3$ and $R^4$ are hydrogen atoms;
a carbamate compound, wherein $R^5$ is a C1-C3 alkyl group optionally having one or more halogen atoms, and $R^2$, $R^3$ and $R^4$ are hydrogen atoms;
a carbamate compound, wherein $R^5$ is a C3-C4 cycloalkyl group optionally having one or more halogen atoms, and $R^2$, $R^3$ and $R^4$ are hydrogen atoms;
a carbamate compound, wherein $R^5$ is a C1-C3 alkoxy group optionally having one or more halogen atoms, and $R^2$, $R^3$ and $R^4$ are hydrogen atoms;
a carbamate compound, wherein $R^1$ is a hydrogen atom, $R^2$ is a C1-C3 alkyl group optionally having one or more halogen atoms, $R^3$, $R^4$ and $R^5$ are hydrogen atoms, and m is 1;
a carbamate compound, wherein $R^1$ is a hydrogen atom, $R^2$, $R^3$, $R^4$ and $R^5$ are hydrogen atoms or methyl groups, $Z^1$ is a methyl group or an ethyl group, and m is 1;
a carbamate compound, wherein $R^1$ is a hydrogen atom, $R^2$ is a methyl group, $R^3$, $R^4$ and $R^5$ are hydrogen atoms, $Z^1$ is a methyl group, and m is 1;

a carbamate compound, wherein $R^1$ is a hydrogen atom, $R^2$ is a methyl group, $R^3$, $R^4$, and $R^5$ are hydrogen atoms, $Z^1$ is a methyl group or an ethyl group, and m is 1; and a carbamate compound, wherein $R^1$ is a hydrogen atom, $R^2$ is a methyl group, $R^3$, $R^4$, and $R^5$ are hydrogen atoms, $Z^1$ is a methyl group, and m is 1.

The carbamate compounds of the present invention can be produced by the following Production Methods.

Production Method A

One of the carbamate compounds of the present invention can be produced by reacting a compound represented by formula (A1) (hereinafter referred to as Compound (A1)) with a compound represented by formula (A2) (hereinafter referred to as Compound (A2)) in the presence of a base and a palladium catalyst.

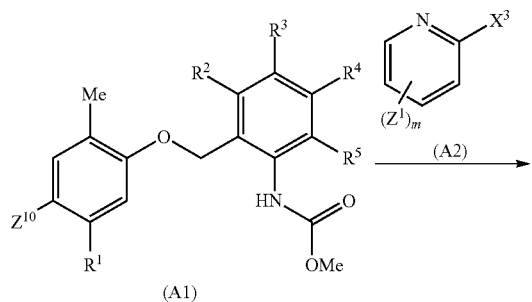

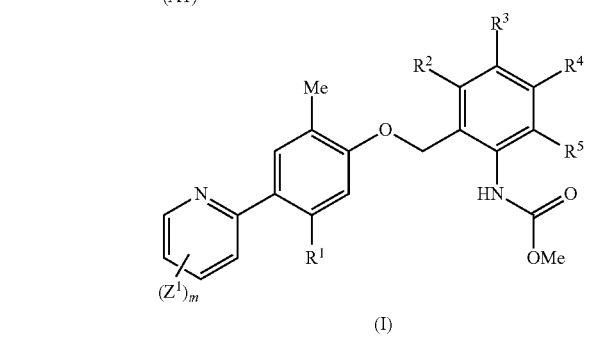

wherein, $X^3$ represents a chlorine atom, a bromine atom or an iodine atom, $Z^{10}$ represents a di(C1-C3 alkoxy)boranyl group or a 4,4,5,5-tetramethyl-1,3,2-dioxaboran-2-yl group, $R^1$, $R^2$, $R^3$, $R^4$, $R^5$, $Z^1$ and m have the same meanings as defined above.

The reaction is usually carried out in a solvent. Examples of the solvent include hydrocarbons such as hexane, cyclohexane, toluene, and xylene; ethers such as diethyl ether, tetrahydrofuran, 1,4-dioxane, ethylene glycol dimethyl ether, anisole, methyl tert-butyl ether and diisopropyl ether; halogenated hydrocarbons such as chloroform, 1,2-dichloroethane and chlorobenzene; acid amides such as N,N-dimethylformamide, 1,3-dimethyl-2-imidazolidinone and N-methylpyrrolidone; esters such as ethyl acetate and methyl acetate; sulfoxides such as dimethyl sulfoxide; nitriles such as acetonitrile and propionitrile; ketones such as acetone, ethyl methyl ketone and isobutyl methyl ketone; water and mixture thereof.

Examples of the palladium catalyst include palladium(II) acetate, tetrakis(triphenyphospine)palladium(0), tris(dibenzylideneacetone)-dipalladium(0) and [1,1'-bis(dipheylphosphino)ferrocene]palladium(II) dichloride dichloromethane adduct.

Examples of the base include alkali metal carbonates such as lithium carbonate, sodium carbonate, potassium carbonate and cesium carbonate; alkali metal hydrogen carbonates such as lithium hydrogen carbonate, sodium hydrogen carbonate, potassium hydrogen carbonate, cesium hydrogen carbonate; alkali metal acetate such as potassium acetate and potassium phosphate tribasic.

In the reaction, usually, 1 to 10 moles of Compound (A2) is used 0.0001 to 1 mole of the palladium catalyst is used of and 1 to 10 moles of the base is used per mole of Compound (A1).

The reaction temperature of the reaction is usually within a range of 0 to 150° C. and the reaction time is usually within a range of 0.1 to 24 hours.

After the completion of the reaction, the carbamate compound of the present invention can be isolated by carrying out post-treatment operation such as extracting the reaction mixture by using an organic solvent, drying the organic layer, and condensing the organic layer.

Production Method B

Another carbamate compound of the present invention can be produced by reacting a compound represented by formula (B1) (hereinafter referred to as Compound (B1)) with methyl chloroformate.

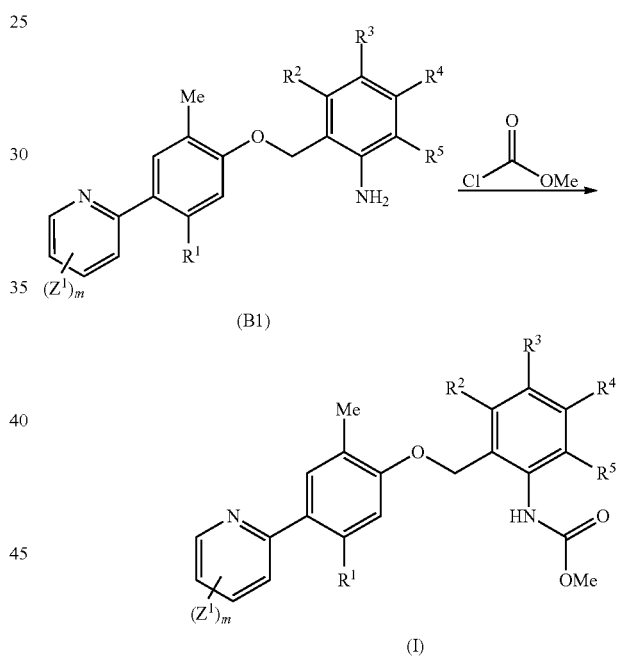

wherein, $R^1$, $R^2$, $R^3$, $R^4$, $R^5$, $Z^1$ and m have the same meanings as defined above.

The reaction is usually carried out in a solvent. Examples of the solvent include hydrocarbons, ethers, halogenated hydrocarbons, acid amides, esters, sulfoxides, nitriles, ketones, and water and mixture thereof as described in Production Method A.

In the reaction, usually, 1 to 10 moles of methyl chloroformate is used per mole of Compound (B1).

The reaction temperature of the reaction is usually within a range of −20 to 150° C. and the reaction time is usually within a range of 0.1 to 24 hours.

To the reaction, organic bases such as triethylamine, N,N'-diisopropylethylamine and pyridine; bases such as alkali metal carbonate and alkali metal hydrogen carbonate may be added, and 0.05 to 5 moles of the base is usually used per mole of Compound (B1).

After the completion of the reaction, the carbamate compound of the present invention can be isolated by carrying out post-treatment operation such as extracting the reaction mixture by using an organic solvent, drying the organic layer, and condensing the organic layer.

The process for producing Intermediate compound will be described.

Reference Production Method A-1

Compound (A1) can be produced by reacting a compound represented by formula (A3) (hereinafter referred to as Compound (A3)) with a boron compound in the presence of a palladium catalyst in accordance with the Miyaura-Ishiyama Borylation reaction. It can be also referred to Angewandte Chemie, International Edition, 46, 5359-5363 (2007).

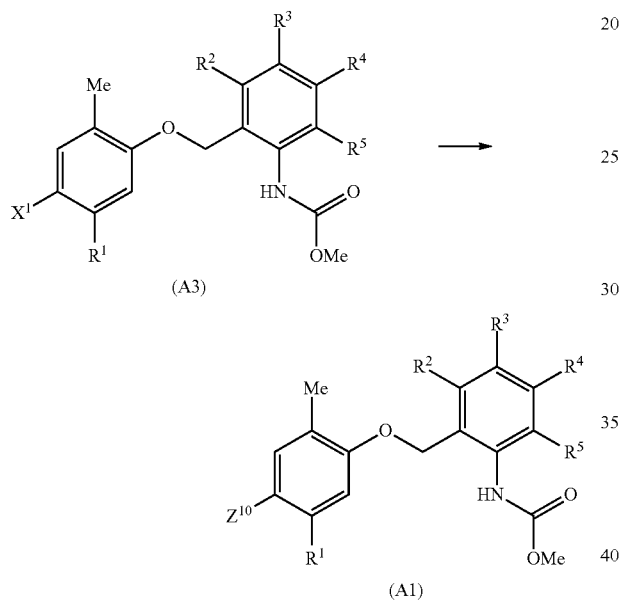

wherein, $X^1$ represents a chlorine atom, a bromine atom or an iodine atom, and $R^1$, $R^2$, $R^3$, $R^4$, $R^5$ and $Z^{10}$ have the same meanings as defined above.

Reference Production Method A-2

Compound (A3) can be produced by reacting a compound represented by formula (A4) (hereinafter referred to as Compound (A4)) with methyl chloroformate in the same manner as Production Method B.

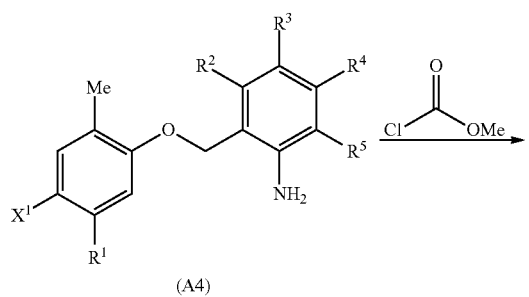

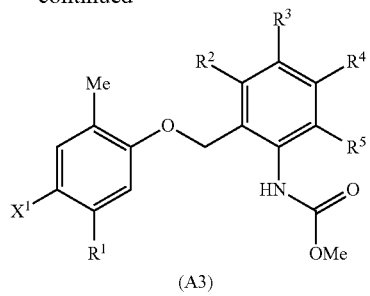

wherein, $R^1$, $R^2$, $R^3$, $R^4$, $R^5$, and $X^1$ have the same meanings as defined above.

Reference Production Method A-3

Compound (A4) can be produced by reacting a compound represented by formula (A5) (hereinafter referred to as Compound (A5)) with a reducing agent in the presence of a catalyst.

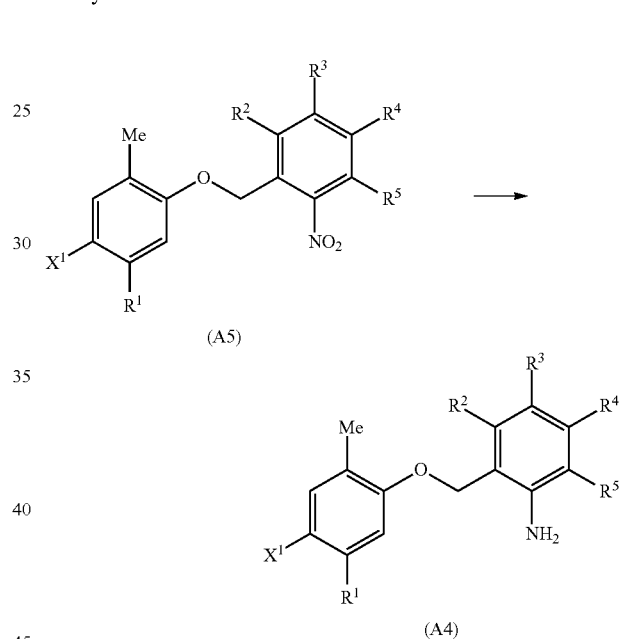

wherein, $R^1$, $R^2$, $R^3$, $R^4$, $R^5$, and $X^1$ have the same meanings as defined above.

The reaction is usually carried out in a solvent. Examples of the solvent include hydrocarbons such as hexane, cyclohexane, toluene, and xylene; ethers such as diethyl ether, tetrahydrofuran, 1,4-dioxane, ethylene glycol dimethyl ether, anisole, methyl tert-butyl ether and diisopropyl ether; halogenated hydrocarbons such as chloroform, 1,2-dichloroethane and chlorobenzene; alcohols such as methanol, ethanol, propanol and butanol; and mixture thereof.

Examples of the reducing agent include potassium borohydride and sodium borohydride.

Examples of the catalyst include copper(I) chloride, iron powder and palladium.

In the reaction, the reducing agent is usually used in the portion within a range of 1 to 10 moles and the catalyst is usually used in the portion within a range of 0.5 to 10 moles, based on 1 mole of Compound (A5).

The reaction temperature of the reaction is usually within a range of −20 to 150° C. and the reaction time is usually within a range of 0.1 to 24 hours.

After the completion of the reaction, Compound (A4) can be isolated by carrying out post-treatment operation such as extracting the reaction mixture by using an organic solvent, drying the organic layer, and condensing the organic layer.

Reference Production Method A-4

Compound (A5) can be produced by reacting a compound represented by formula (A6) (hereinafter referred to as Compound (A6)) with a compound represented by formula (A7) (hereinafter referred to as Compound (A7)) in the presence of a base.

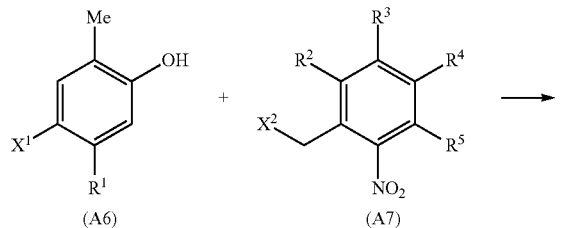

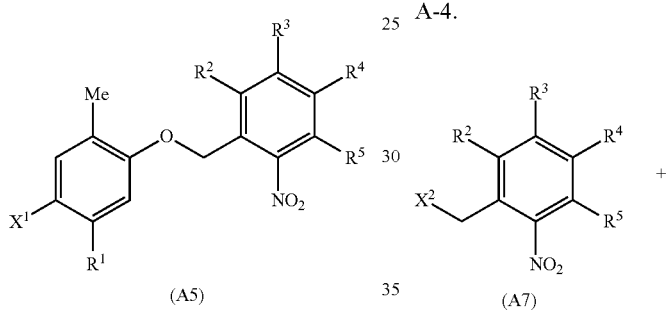

wherein, $X^2$ represents a leaving group such as a chlorine atom, a bromine atom, an iodine atom, a mesyloxy group or a tosyloxy group, and $R^1$, $R^2$, $R^3$, $R^4$, $R^5$ and $X^1$ have the same meanings as defined above.

The reaction can be carried out in accordance with Production Method N of US Patent Application Publication No. 2015/203511.

Reference Production Method B-1

Compound (B1) can be produced by reacting a compound represented by formula (B2) (hereinafter referred to as Compound (B2)) with the reducing agent in the presence of the catalyst in the same manner as Reference Production Method A-3.

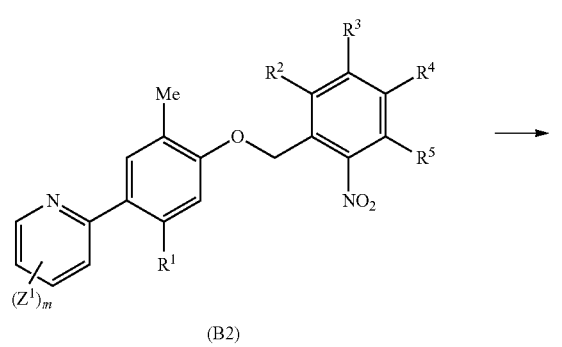

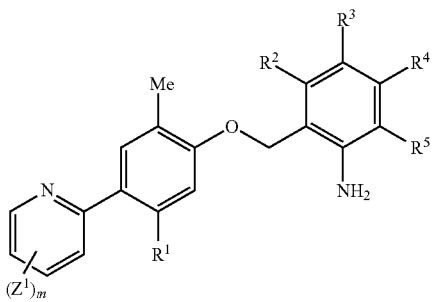

wherein, $R^1$, $R^2$, $R^3$, $R^4$, $R^5$, $Z^1$ and m have the same meanings as defined above.

Reference Production Method B-2

Compound (B2) can be produced by reacting Compound (A7) with a compound represented by formula (B3) (hereinafter referred to as Compound (B3)) in the presence of a base in the same manner as Reference Production Method A-4.

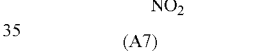

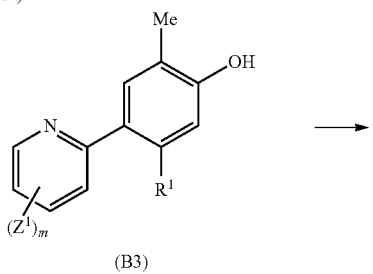

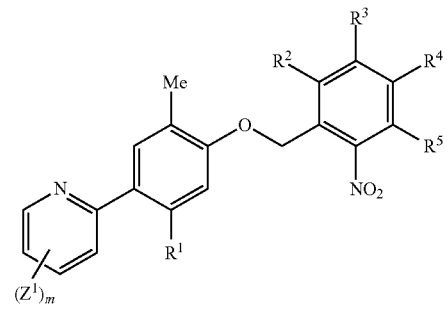

wherein, $R^1$, $R^2$, $R^3$, $R^4$, $R^5$, $X^2$, $Z^1$ and m have the same meanings as defined above.

Reference Production Method B-3

Compound (B3) can be produced by reacting a compound represented by formula (B4) (hereinafter referred to as Compound (B4)) with a protic acid.

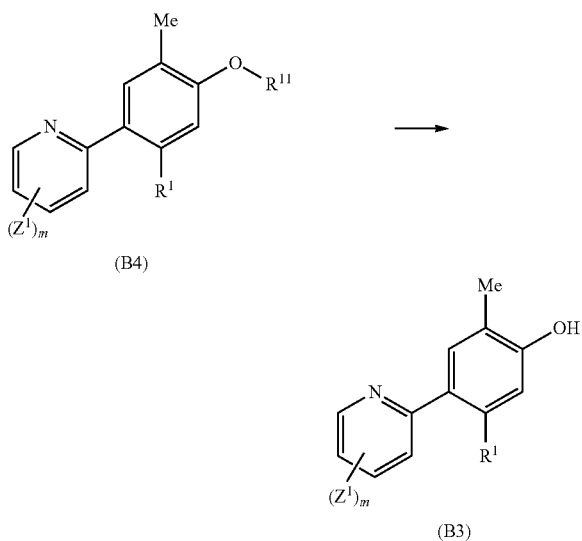

(B4)

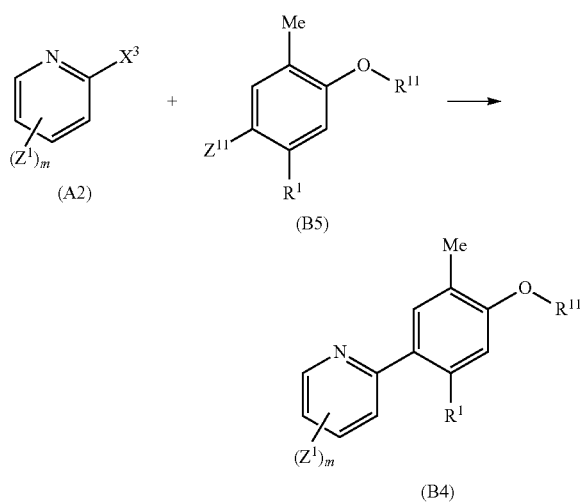

(B3)

wherein, $R^{11}$ represents a C1-C5 alkyl group, and $R^1$, $Z^1$ and m have the same meanings as defined above.

The reaction is usually carried out in a solvent. Examples of the solvent include alcohols such as methanol, ethanol, propanol and butanol; water; acetic acid, and mixture thereof.

Examples of the protic acids include hydrochloric acid, hydrobromic acid and sulfuric acid.

In the reaction, a large excess amount of the protic acid is usually used.

The reaction temperature of the reaction is usually within a range of −20 to 150° C. and the reaction time is usually within a range of 0.1 to 100 hours.

After the completion of the reaction, Compound (B3) can be isolated by carrying out post-treatment operation such as extracting the reaction mixture by using an organic solvent, drying the organic layer, and condensing the organic layer.

Reference Production Method B-4

Compound (B4) can be produced by reacting a compound represented by formula (B5) (hereinafter referred to as Compound (B5)) with Compound (A2) in the presence of a base and a palladium catalyst in the same manner as Production Method A.

wherein, $Z^{11}$ represents a di(C1-C3 alkoxy)boranyl group, a 4,4,5,5-tetramethyl-1,3,2-dioxaboran-2-yl group or a borono group, $R^1$, $R^{11}$, $X^3$, $Z^1$ and m have the same meanings as defined above.

Each compound produced in accordance with the above Production Methods and Reference Production Methods can be further purified by known means such as crystallization, recrystallization and chromatography.

Although the carbamate compound of the present invention can be use as it is, the carbamate compound is usually used after being mixed with any of solid carriers, liquid carriers, surfactants, and the like, and optionally adding any of auxiliary agents for formulation, such as stickers, dispersers, and stabilizers, to the carbamate compound in order to formulate wettable powders, water dispersible granules, flowables, granules, dry flowables, emulsifiable concentrates, aqueous solutions, oil solutions, smoking agents, aerosols, microcapsules, or the like. In these formulations, the carbamate compound of the present invention is usually included in an amount of 0.1 to 99% by weight, preferably 0.2 to 90% by weight.

Examples of the solid carriers include clays (for example, kaolin, diatomaceous earth, synthetic hydrated silicon dioxide, Fubasami clay, bentonite, and acid clay), talcs, pyrophyllite or other inorganic minerals (for example, sericite, quartz powder, sulfur powder, activated charcoal, calcium carbonate, and hydrated silica) in the form of fine powders or particulates, and examples of the liquid carries include water, alcohols, ketones, hydrocarbons, esters, nitriles, ethers, acid amides and halogenated hydrocarbons.

Examples of the surfactants include alkyl sulfates, alkyl sulfonates, alkyl aryl sulfonates, alkyl aryl ethers, and polyoxyethylenated compounds thereof, polyoxyethylene glycol ethers, polyhydric alcohol esters, and sugar alcohol derivatives.

Examples of other auxiliary agents for formulation include sticking agents, dispersing agents and stabilizers, specifically casein, gelatin, polysaccharides (such as starch, gum arabic, cellulose derivatives and alginic acid), lignin derivatives, bentonite, sugars, water-soluble synthetic polymers (such as polyvinyl alcohols, polyvinylpyrrolidones, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof, and the like.

The said formulated carbamate compound of the present invention may be diluted with water or the like at the time of application thereof; however, in which case, the formulated carbamate compound may be applied after being mixed with any of spreading agents such as oils, such as mineral oils and vegetable oils, and surfactants. Specific examples of the spreading agents, which can be used as the mixture, include Nimbus®, Assist®, Aureo®, Iharol®, Silwet L-77®, BreakThru®, Sundance II®, Induce®, Penetrator®, AgriDex®, Lutensol A8®, NP-7®, Triton®, Nufilm®, Emulgator NP7®, Emulad®, TRITON X 45®, AGRAL 90®, AGROTIN®, ARPON®, EnSpray N®, BANOLE®, and the like.

The method for applying the carbamate compound of the present invention are not particularly limited, and includes, for example, an application to plants such as a foliage application; an application to soil such as seed disinfection; and an application to area for cultivating plants such as a submerged treatment.

The carbamate compound of the present invention can be used as an agent for controlling plant diseases in agricultural lands such as fields, paddy fields, lawns and orchards, and can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), ammiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, and the like;

Flowers,

Ornamental foliage plants,

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, and the like; Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea*, and *Taxus cuspidate*); and the like.

The above-mentioned "plants" include genetically modified crops.

Examples of plant diseases include plant diseases caused by filamentous fungus, bacteria, virus and the like, and the specific examples are shown below; however, the plant diseases are not limited thereto.

Examples of plant diseases controllable by the present invention include such as fungal diseases. More specifically, the following plant diseases are listed; however, the diseases are not limited thereto.

Rice diseases: rice blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhulasnow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora triticirepentis*), seeding blight caused by the genus *Rhizoctonia* (*Rhizoctonia solani*), and take all disease (*Gaeumannomyces graminis*); Barley diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and seeding blight caused by the genus *Rhizoctonia* (*Rhizoctonia solani*); Corn diseases: rust (*Puccinia sorghi*), southern rust (*Puccinia polysora*), northern leaf blight (*Setosphaeria turcica*), topical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), and phaeosphaeria leaf spot (*Phaeosphaeria maydis*), diplodia disease (*Stenocarpella maydis, Stenocarpella macrospora*), Stalk rot disease (*Fusarium graminearum, Fusarium verticilioides, Colletotrichum graminicola*), leaf and stem smut (*Ustilago maydis*); Cotton diseases: anthracnose (*Colletotrichum gossypii*), grey mildew (*Ramuraria areola*), and alternaria leaf spot (*Alternaria macrospora, A. gossypii*); black root rot caused by *Thielaviopsis* species (*Thielaviopsis basicola*); Coffee diseases: rust (*Hemileia vastatrix*), leaf spot disease (*Cercospora coffeicola*); Rapeseed diseases: sclerotinia rot (*Sclerotinia sclerotiorum*), black spot (*Alternaria brassicae*), and black leg (*Phoma lingam*); Sugar cane disease: rust ((*Puccinia melanocephela, Puccinia kuehnii*), smut (*Ustilago scitaminea*); Sunflower disease: rust (*Puccinia helianthi*), downey mildew (*Plasmopara halstedii*); Citrus diseases: melanose (*Diaporthe citri*), scab (*Elsinoe fawcetti*), and fruit rot (*Penicillium digitatum, P. italicum*); Phytophthora rot (*Phytophthora parasitica, Phytophthora citrophthora*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Glomerella cingulata*), brown spot (*Diplocarpon mali*), black rot (*Botryosphaeria berengeriana*); phytophthora rot (*Phytophtora cactorum*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and Phomopsis rot (*Phomopsis* sp.); Grapes diseases: anthracnose (*Elsinoe ampelina*), ripe rot (*Glomerella cingulata, Colletotrichum acutatum*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans*); Eggplant diseases: brown spot (*Phomopsis vexans*) and powdery mildew (*Erysiphe cichoracearum*); Cruciferous vegetables diseases: alternaria leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrithum glycines, C. truncatum*), *Rhizoctonia* aerial blight (*Rhizoctonia solani*), septoria brown spot (*Septoria glycines*), and frog eye leaf spot (*Cercospora sojina*); sclerotinia rot (*Sclerotinia sclerotio-* rum), powdery mildew (*Microspaera diffusa*), *phytophthora* rot (*Phytophthora sojae*), downey mildew (*Peronospora manshurica*), sudden death disease (*Fusarium virguliforme*); Kidney beans diseases: stem rot (*Sclerotinia sclerotiorum*), watery soft rot (*Sclerotinia sclerotiorum*), rust (*Uromyces appendiculatus*), angular leaf spot (*Phaeoisariopsis griseola*), anthracnose (*Colletotrichum lindemthianum*); Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), pink rot (*Phytophthora erythroseptica*), powdery scab (*Spongospora subterranean* f. sp. *subterranean*), verticilliun wilt (*Verticillium alboatrum, V. dahlia, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theaesinensis*); Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: *cercospora* leaf spot (*Cercospora beticola*), leaf blight (*Thanatephorus cucumeris*), root rot (*Thanatephorus cucumeris*), and *aphanomyces* root rot (*Aphanomyces cochlioides*); Rose diseases: black spot (*Diplocarpon rosae*) and powdery mildew (*Sphaerotheca pannosa*); Chrysanthemum diseases: leaf blight (*Septoria chrysanthemiindici*) and white rust (*Puccinia horiana*); Onion diseases: *botrytis* leaf blight (*Botrytis cinerea, B. byssoidea, B. squamosa*), gray-mold neck rot (*Botrytis slli*), and small sclerotial rot (*Botrytis squamosa*); various crops diseases: gray mold (*Botrytis cinerea*) and *sclerotinia* rot (*Sclerotinia sclerotiorum*); Japanese radish diseases: alternaria leaf spot (*Alternaria brassicicola*); Turfgrass diseases: dollar spot (*Sclerotinia homeocarpa*) and brown patch and large patch (*Rhizoctonia solani*); and Banana diseases: Sigatoka disease (*Mycosphaerella fijiensis, Mycosphaerella musicola*).

Seed diseases and early growth disease of various crops are caused by *Aspergillus, Penicillium, Fusarium, Gibberella, Tricoderma, Thielaviopsis, Rhizopus, Mucor, Corticium, Phoma, Rhizoctonia* and *Diplodia*.

Bacterial seedling blight of rice; Bacterial spot of cucumber; Bacterial wilt of eggplant; Bacterial canker of Citrus and Bacterial soft rot of Chinese cabbage.

Virus diseases of various diseases mediated by Polymixa and Olpidium.

EXAMPLES

The present invention will be described in more detail below by way of Production Examples, Reference Production Examples, Formulation Examples and Test Examples; however, the present invention is not limited to these Examples.

$^1$H-NMR means a proton nuclear magnetic resonance spectrum, in which tetramethylsilane is used as an internal standard material, and chemical shifts (δ) are indicated in ppm.

Production Example 1

A mixture of 0.41 g of Intermediate (16A) described in the following Reference Production Example 7, 0.34 g of 2-bromo-5-methylpyridine, 0.02 g of [1,1'-bis(diphenylphosphino)ferrocene] palladium(II) dichloride dichloromethane adduct, 0.64 g of potassium phosphate tribasic, 4 ml of 1,2-dimethoxyethane and 0.4 ml of water was stirred at 85° C. for 4 hours. After the reaction mixture was cooled, the residue was obtained by being condensed and was subjected to silica gel column chromatography to give 0.16 g of a compound represented by the following formula (hereinafter referred to as the present Compound 1).

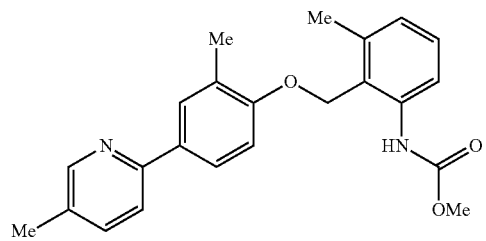 [SMILES: COC(=O)Nc1cccc(C)c1COc1ccc(-c2ccc(C)cn2)cc1C]

$^1$H-NMR (CDCl$_3$) δ: 8.49 (1H, s), 7.84-7.82 (1H, m), 7.82-7.75 (2H, m), 7.63-7.51 (3H, m), 7.30-7.28 (1H, m), 7.07 (1H, d), 6.99 (1H, d), 5.15 (2H, s), 3.75 (3H, s), 2.42 (3H, s), 2.36 (3H, s), 2.29 (3H, s).

Compounds represented by formula (a):

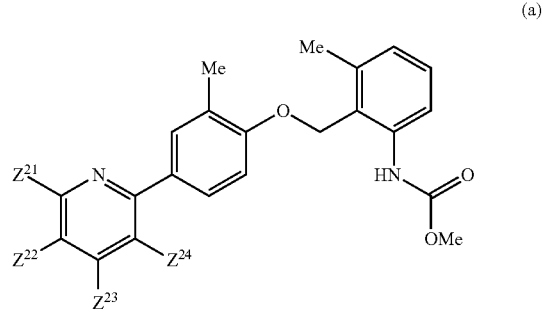

(a)

have $Z^{21}$, $Z^{22}$, $Z^{23}$ and $Z^{24}$, and their physical property values are as shown in Table 1, produced in accordance with Production Example 1.

TABLE 1

|  | $Z^{21}$ | $Z^{22}$ | $Z^{23}$ | $Z^{24}$ |
| --- | --- | --- | --- | --- |
| Present Compound 2 | H | H | Me | H |
| Present Compound 3 | H | H | H | Me |
| Present Compound 4 | Et | H | H | H |

The present Compound 2:
$^1$H-NMR (CDCl$_3$) δ: 8.52 (1H, d), 7.88-7.75 (3H, m), 7.58-7.47 (2H, m), 7.30-7.27 (1H, m), 7.08 (1H, d), 7.03-6.98 (2H, m), 5.16 (2H, s), 3.75 (3H, s), 2.42 (3H, s), 2.41 (3H, s), 2.30 (3H, s).

The present Compound 3:
$^1$H-NMR (CDCl$_3$) δ: 8.53-8.50 (1H, m), 7.79 (1H, brs), 7.63-7.53 (2H, m), 7.41-7.36 (2H, m), 7.30-7.27 (1H, m), 7.16 (1H, dd), 7.06 (1H, d), 6.99 (1H, d), 5.15 (2H, s), 3.76 (3H, s), 2.42 (3H, s), 2.40 (3H, s), 2.28 (3H, s).

The present Compound 4:
$^1$H-NMR (CDCl$_3$) δ: 7.86-7.75 (3H, m), 7.64 (1H, t), 7.55 (1H, brs), 7.48 (1H, d), 7.30-7.27 (1H, m), 7.07 (2H, d), 6.99 (1H, d), 5.15 (2H, s), 3.75 (3H, s), 2.89 (2H, q), 2.42 (3H, s), 2.30 (3H, s), 1.37 (3H, t).

Production Example 2

A mixture of 0.42 g of Intermediate (7A) described in the following Reference Production Example 7, 0.26 g of potassium carbonate, 6 ml of tetrahydrofuran was cooled with ice, followed by addition of 0.11 ml of methyl chloroformate to the mixture. The reaction solution was stirred at room temperature for 3 hours. The residue obtained by being condensed under reduced pressure was subjected to a silica gel chromatography to give 0.49 g of a compound (hereinafter referred to as the present Compound 5) represented by the following formula.

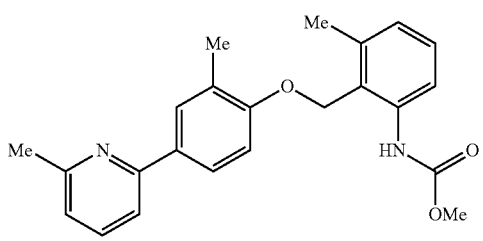 [SMILES: COC(=O)Nc1cccc(C)c1COc1ccc(-c2cccc(C)n2)cc1C]

$^1$H-NMR (CDCl$_3$) δ: 7.85-7.74 (3H, m), 7.63-7.51 (2H, m), 7.47 (1H, d), 7.30-7.26 (1H, m), 7.08-7.05 (2H, m), 6.99 (1H, d), 5.15 (2H, s), 3.75 (3H, s), 2.62 (3H, s), 2.42 (3H, s), 2.30 (3H, s).

Reference Production Examples of production intermediates will be described below.

Reference Production Example 1

A mixture of 4.0 g of 2-(bromomethyl)-3-methylnitrobenzene, 2.4 g of 4-bromo-2-methylphenol, 4.8 g of potassium carbonate and 40 ml of acetonitrile was heated to reflux for 5 hours. The reaction solution was filtered through Celite®. The residue obtained by condensing the filtrate under reduced pressure was subjected to silica gel chromatography to give 3.2 g of the following Intermediate (1A).

The compounds produced in accordance with Reference Production Example 1 and their physical property values will be shown below.

The compounds represented by formula (aA):

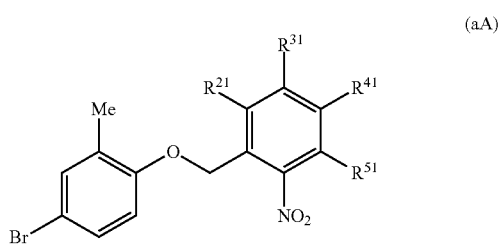

have R$^{21}$, R$^{31}$, R$^{41}$ and R$^{51}$ that are shown in Table 2.

TABLE 2

|  | R$^{21}$ | R$^{31}$ | R$^{41}$ | R$^{51}$ |
| --- | --- | --- | --- | --- |
| Intermediate (1A) | Me | H | H | H |
| Intermediate (2A) | H | H | H | H |
| Intermediate (3A) | H | Me | H | H |
| Intermediate (4A) | H | H | Me | H |
| Intermediate (5A) | H | H | H | Me |

Intermediate (1A)
$^1$H-NMR (DMSO-d$_6$) δ: 7.74 (1H, d), 7.62 (1H, d), 7.53 (1H, t), 7.39-7.32 (2H, m), 7.04 (1H, d), 5.20 (2H, s), 2.50 (3H, s), 2.03 (3H, s).

Intermediate (2A)
$^1$H NMR (CDCl$_3$) δ: 8.17 (1H, d), 7.87 (1H, d), 7.70 (1H, t), 7.51 (1H, t), 7.31 (1H, d), 7.24 (1H, d), 6.74 (1H, d), 5.46 (2H, s), 2.31 (3H, s).

Intermediate (3A)
$^1$H-NMR (CDCl$_3$) δ: 8.10 (1H, d), 7.65 (1H, s), 7.34-7.21 (3H, m), 6.75 (1H, d), 5.44 (2H, s), 2.47 (3H, s), 2.31 (3H, s).

Intermediate (4A)
$^1$H-NMR (CDCl$_3$) δ: 7.98 (1H, s), 7.71 (1H, d), 7.49 (1H, d), 7.32-7.18 (2H, m), 6.72 (1H, d), 5.41 (2H, s), 2.46 (3H, s), 2.29 (3H, s).

Intermediate (5A)
$^1$H NMR (CDCl$_3$) δ: 7.50-7.38 (2H, m), 7.32-7.18 (3H, m), 6.67 (1H, d), 5.09 (2H, s), 2.39 (3H, s), 2.22 (3H, s).

Reference Production Example 2

A mixture of 3.2 g of Intermediate (1A), 2.9 g of copper(I) chloride, 50 ml of methanol was cooled with ice, followed by addition of 3.3 g of potassium borohydride to the mixture, and was stirred for 1 hour while being cooled with ice, followed by filtration through Celite®. To the residue obtained by condensing the filtrate under reduced pressure, ethyl acetate was added; and the mixture was washed with an aqueous saturated sodium hydrogen carbonate solution. The organic layer was dried over anhydrous magnesium sulfate, and concentrated under reduced pressure to give 2.0 g of the following Intermediate (6A).

The compounds produced in accordance with Reference Production Example 2 and their physical property values will be shown below.

The compounds represented by formula (bA):

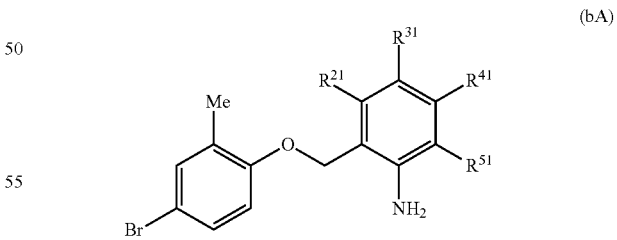

have R$^{21}$, R$^{31}$, R$^{41}$ and R$^{51}$ that are shown in Table 3.

TABLE 3

|  | R$^{21}$ | R$^{31}$ | R$^{41}$ | R$^{51}$ |
| --- | --- | --- | --- | --- |
| Intermediate (6A) | Me | H | H | H |
| Intermediate (7A) | H | H | H | H |
| Intermediate (8A) | H | Me | H | H |

TABLE 3-continued

|  | $R^{21}$ | $R^{31}$ | $R^{41}$ | $R^{51}$ |
|---|---|---|---|---|
| Intermediate (9A) | H | H | Me | H |
| Intermediate (10A) | H | H | H | Me |

Intermediate (6A)

$^{1}$H-NMR (CDCl$_{3}$) δ: 7.32-7.25 (2H, m), 7.07 (1H, t), 6.88 (1H, d), 6.68-6.56 (2H, m), 5.03 (2H, s), 3.96 (2H, brs), 2.34 (3H, s), 2.16 (3H, s).

Intermediate (7A)

$^{1}$H NMR (DMSO-d$_{6}$) δ: 7.36-7.28 (2H, m), 7.22-7.16 (1H, m), 7.06-6.97 (2H, m), 6.67 (1H, d), 6.60-6.54 (1H, m), 5.05 (2H, brs), 4.96 (2H, s), 2.17 (3H, s).

Intermediate (8A)

$^{1}$H-NMR (DMSO-d$_{6}$) δ: 7.33-7.20 (2H, m), 6.99 (2H, d), 6.79-6.88 (1H, m), 6.65 (1H, d), 4.97 (2H, s), 3.91 (2H, brs), 2.26 (3H, s), 2.19 (3H, s).

Intermediate (9A)

$^{1}$H-NMR (CDCl$_{3}$) δ: 7.30-7.21 (2H, m), 7.07 (1H, d), 6.83 (1H, d), 6.62-6.49 (2H, m), 4.98 (2H, s), 3.95 (2H, brs), 2.27 (3H, s), 2.18 (3H, s).

Intermediate (10A)

$^{1}$H-NMR (DMSO-d$_{6}$) δ: 7.26-7.21 (2H, m), 7.21-7.01 (2H, m), 6.90-6.81 (1H, s), 6.70 (1H, t), 5.02 (2H, s), 4.05 (2H, brs), 2.20 (3H, s), 2.19 (3H, s).

Reference Production Example 3

In the method described in Production Example 2, Intermediate (6A) was used instead of Intermediate (26A) to give the following Intermediate (11A).

The compounds produced in accordance with Reference Production Example 5 and their physical property values will be shown below.

The compounds represented by formula (cA):

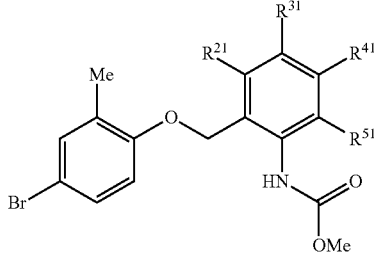

(cA)

have $R^{21}$, $R^{31}$, $R^{41}$ and $R^{51}$ that are shown in Table 4.

TABLE 4

|  | $R^{21}$ | $R^{31}$ | $R^{41}$ | $R^{51}$ |
|---|---|---|---|---|
| Intermediate (11A) | Me | H | H | H |
| Intermediate (12A) | H | H | H | H |
| Intermediate (13A) | H | Me | H | H |
| Intermediate (14A) | H | H | Me | H |
| Intermediate (15A) | H | H | H | Me |

Intermediate (11A)

$^{1}$H-NMR (DMSO-d$_{6}$) δ: 9.07 (1H, brs), 7.30-7.38 (2H, m), 7.25 (2H, d), 7.12-6.96 (2H, m), 5.05 (2H, s), 3.60 (3H, s), 2.35 (3H, s), 2.06 (3H, s).

Intermediate (12A)

$^{1}$H-NMR (DMSO-d$_{6}$) δ: 9.0 (1H, brs), 7.47 (2H, t), 7.40-7.22 (3H, m), 7.25-7.16 (1H, m), 6.92 (1H, d), 5.12 (2H, s), 3.65 (3H, s), 2.17 (3H, s).

Intermediate (13A)

$^{1}$H-NMR (DMSO-d$_{6}$) δ: 8.89 (1H, brs), 7.38-7.23 (4H, m), 7.16-7.08 (1H, m), 6.92 (1H, d), 5.07 (2H, s), 3.63 (3H, s), 2.28 (3H, s), 2.16 (3H, s).

Intermediate (14A)

$^{1}$H NMR (DMSO-d$_{6}$) δ: 8.93 (1H, brs), 7.35-7.30 (4H, m), 6.98 (1H, d), 6.90 (1H, d), 5.07 (2H, s), 3.64 (3H, s), 2.29 (3H, s), 2.15 (3H, s).

Intermediate (15A)

$^{1}$H-NMR (DMSO-d$_{6}$) δ: 8.80 (1H, brs), 7.34 (1H, d), 7.31-7.25 (2H, m), 7.26-7.17 (2H, m), 6.86 (1H, d), 5.05 (2H, s), 3.62 (3H, s), 2.20 (3H, s), 2.18 (3H, s).

Reference Production Example 7

A mixture of 0.50 g of Intermediate (11A), 0.42 g of bis-(pinacolato)diboron, 0.40 g of potassium acetate, 10 ml of 1,4-dioxane, 0.06 g of [1,1'-bis-(diphenylphosphino)ferrocene] palladium(II) dichloride dichloromethane adduct was heated to reflux for 16 hours, followed by filtration through Celite®. The residue obtained by condensing the filtrate was subjected to silica gel column chromatography to give 0.35 g of the following Intermediate (16A).

The compounds produced in accordance with Reference Production Example 7 and their physical property values will be shown below.

The compounds represented by formula (dA):

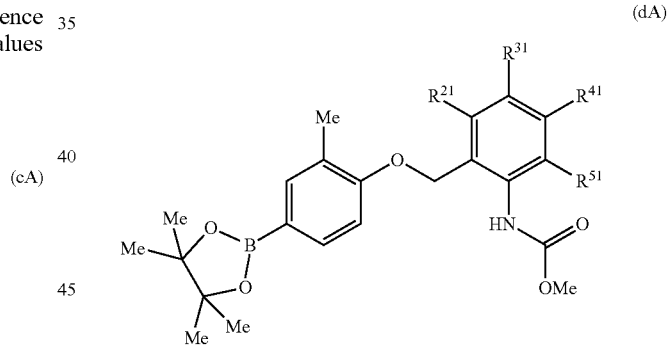

(dA)

have $R^{21}$, $R^{31}$, $R^{41}$ and $R^{51}$ that are shown in Table 5.

TABLE 5

|  | $R^{21}$ | $R^{31}$ | $R^{41}$ | $R^{51}$ |
|---|---|---|---|---|
| Intermediate (16A) | Me | H | H | H |
| Intermediate (17A) | H | H | H | H |
| Intermediate (18A) | H | Me | H | H |
| Intermediate (19A) | H | H | Me | H |
| Intermediate (20A) | H | H | H | Me |

Intermediate (16A)

$^{1}$H-NMR (DMSO-d$_{6}$) δ: 9.08 (1H, brs), 7.51 (1H, d), 7.44 (1H, s), 7.25 (2H, t), 7.12-7.02 (2H, m), 5.09 (2H, s), 3.61 (3H, s), 2.35 (3H, s), 2.07 (3H, s), 1.27 (12H, s).

Intermediate (17A)

$^{1}$H NMR (DMSO-d$_{6}$) δ: 9.01 (1H, brs), 7.42-7.56 (4H, m), 7.38-7.26 (1H, m), 7.24-7.13 (1H, m), 6.97 (1H, d), 5.17 (2H, s), 3.66 (3H, s), 2.19 (3H, s), 1.27 (12H, s).

Intermediate (18A)

$^1$H-NMR (DMSO-d$_6$) δ: 8.89 (1H, brs), 7.48 (2H, d), 7.24-7.36 (2H, m), 7.11 (1H, dd), 6.96 (1H, d), 5.10 (2H, s), 3.63 (3H, s), 2.28 (3H, s), 2.18 (3H, s), 1.27 (12H, s).

Intermediate (19A)

$^1$H-NMR (DMSO-d$_6$) δ: 8.93 (1H, brs), 7.47 (2H, d), 7.32 (2H, t), 6.97 (2H, t), 5.11 (2H, s), 3.64 (3H, s), 2.29 (3H, s), 2.16 (3H, s), 1.27 (12H, s).

Intermediate (20A)

$^1$H-NMR (DMSO-d$_6$) δ: 8.8 (1H, brs), 7.46 (2H, d), 7.31 (1H, dd), 7.25-7.17 (2H, m), 6.91 (1H, d), 5.09 (2H, s), 3.62 (3H, s), 2.20 (3H, s), 2.19 (3H, s), 1.27 (12H, s).

Reference Production Example 5

A mixture of 1.93 g of 4-methoxy-3-methylphenylboronic acid, 2.00 g of 2-bromo-5-methylpyridine, 0.48 g of [1,1'-bis(diphenylphosphino)ferrocene] palladium(II) dichloride dichloromethane adduct, 4.20 g of sodium carbonate, 20 ml of 1,4-dioxane and 1 ml of water was heated to reflux for 16 hours. After being cooled, the reaction mixture was filtered, and the filtrate was extracted with ethyl acetate. The organic layer was washed with water and saturated aqueous sodium chloride, and was dried over anhydrous sodium sulfate, followed by being condensed under reduced pressure. The result residue was subjected to silica gel column chromatography to give 2.20 g of Intermediate (21A) represented by the following formula.

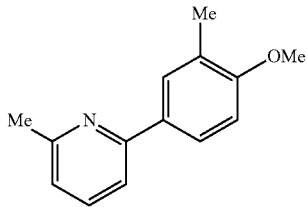 [SMILES: COc1ccc(-c2cccc(C)n2)cc1C]

$^1$H-NMR (CDCl$_3$) δ: 2.29 (3H, s), 2.61 (3H, s), 3.87 (3H, s), 6.89 (1H, d), 7.02 (1H, d), 7.45 (1H, d), 7.58 (1H, t), 7.77 (1H, dd), 7.80 (1H, s).

Reference Production Example 6

A mixture of 2.20 g of Intermediate (21A), 15.4 ml of 48% hydrobromic acid and 15.4 ml of acetic acid was heated to reflux for 8 hours. The reaction solution was concentrated and dried to give 2.10 g of Intermediate (22A) represented by the following formula.

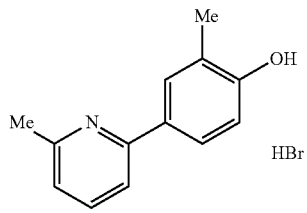

$^1$H-NMR (CDCl$_3$) δ: 2.30 (3H, s), 3.89 (3H, s), 6.92 (1H, d), 7.52 (1H, dd), 7.90-7.81 (4H, m), 10.27 (1H, brs).

Reference Production Example 7

A mixture of 3.50 g of 2-(bromomethyl)-3-methylnitrobenzene, 3.31 g of Intermediate (22A), 4.21 g of potassium carbonate, and 100 ml of acetonitrile was stirred while being heated to reflux for 9 hours. After being cooled, the reaction mixture was filtered through Celite®. The residue obtained by being condensed under reduced pressure was subjected to silica gel column chromatography to give 6.0 g of Intermediate (23A) represented by the following formula.

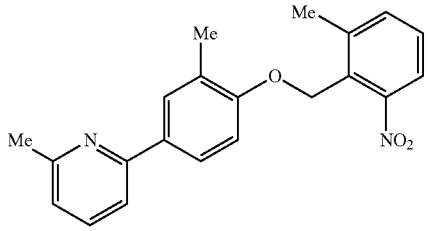

$^1$H-NMR (CDCl$_3$) δ: 7.79-7.77 (2H, m), 7.67 (1H, d), 7.59 (1H, t), 7.49-7.45 (2H, m), 7.40 (1H, t), 7.04 (1H, d), 6.99 (1H, d), 5.28 (2H, s), 2.61 (3H, s), 2.53 (3H, s), 2.22 (3H, s).

Reference Production Example 8

To a solution obtained by adding 10 ml of methanol to 0.77 g of Intermediate (23A), copper(I) chloride was added; and then the solution was cooled with ice. To the solution, 0.72 g of potassium borohydride was added; and the reaction solution was stirred for 2 hours while being cooled with ice, and then was filtrated through Celite®. To the residue obtained by concentration under reduced pressure, ethyl acetate was added; and the mixture was washed with saturate aqueous sodium hydrogen carbonate. The organic layer was concentrated after being dried by using anhydrous magnesium sulfate to give 0.57 g of Intermediate (24A) represented by the following formula.

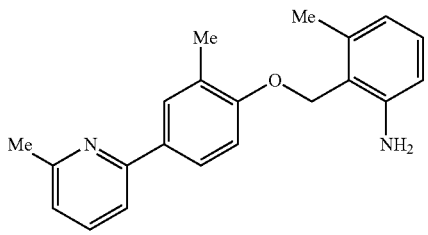 [SMILES: Cc1cccc(-c2ccc(OCc3c(C)cccc3[N+](=O)[O-])c(C)c2)n1]

$^1$H-NMR (CDCl$_3$) δ: 7.84-7.78 (2H, m), 7.60 (1H, t), 7.46 (1H, d), 7.10-7.03 (3H, m), 6.66 (1H, d), 6.62 (1H, d), 5.12 (2H, s), 4.03 (2H, brs), 2.62 (3H, s), 2.38 (3H, s), 2.27 (3H, s).

Compounds HA1001-1 to HA1036-128 could be obtained in accordance with the above-described method.

Compounds HA1001-1 to HA1036-128 are the carbamate compounds, wherein E means any one of substituent numbers 1 to 128, as shown below. In the following [substituent numbers: E], Me represents a methyl group, Et represents an ethyl group, Pr represents a propyl group, iPr represents an isopropyl group, and PYR2 represents a pyridine-2-yl group.

(HA1001)
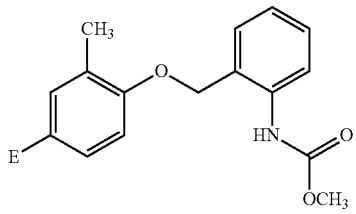
(HA1002)
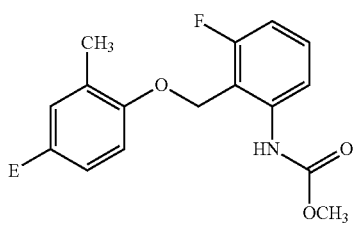
(HA1003)
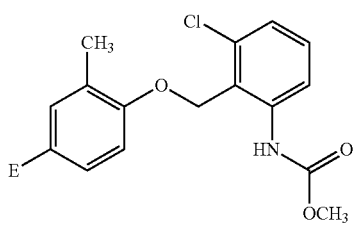
(HA1004)
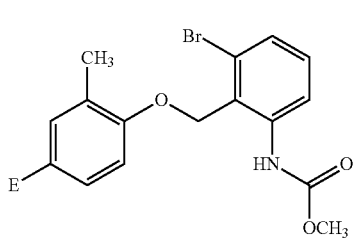
(HA1005)
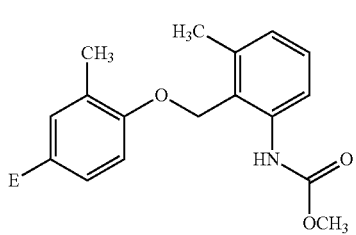
(HA1006)
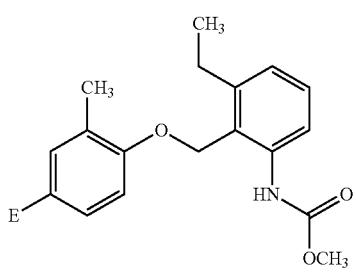
-continued
(HA1007)
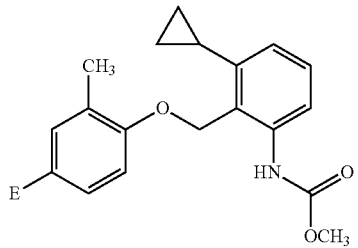
(HA1008)
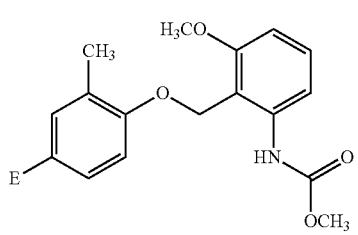
(HA1009)
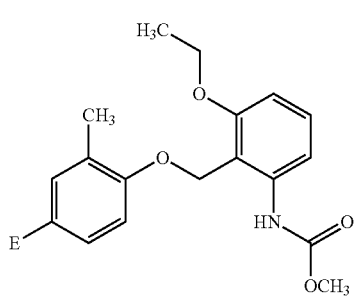
(HA1010)
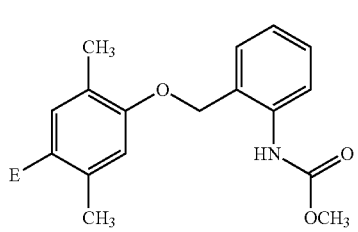
(HA1011)
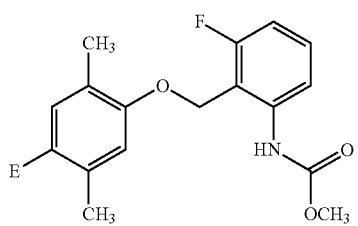
(HA1012)
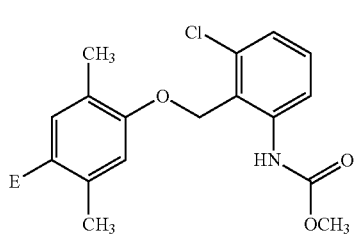

(HA1013)
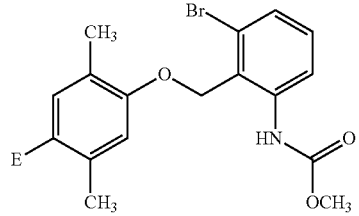
(HA1014)
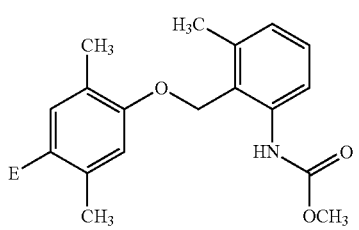
(HA1015)
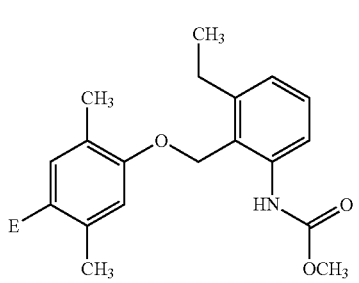
(HA1016)
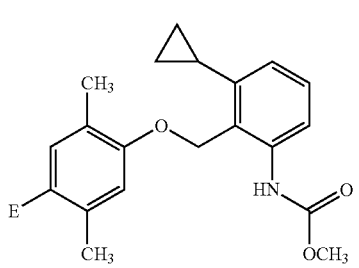
(HA1017)
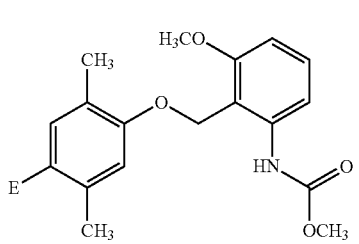
(HA1018)
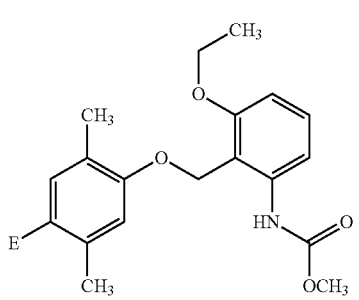
(HA1019)
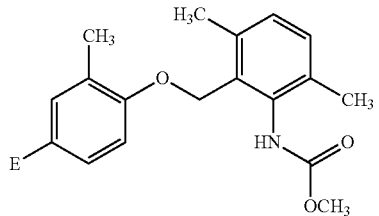
(HA1020)
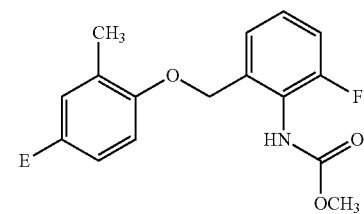
(HA1021)
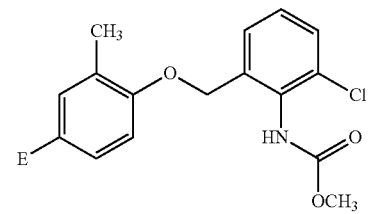
(HA1022)
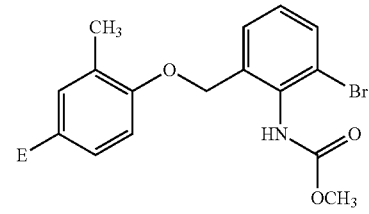
(HA1023)
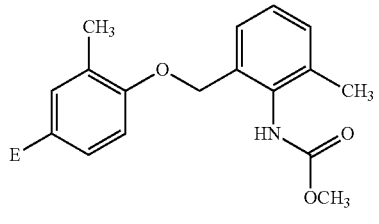
(HA1024)
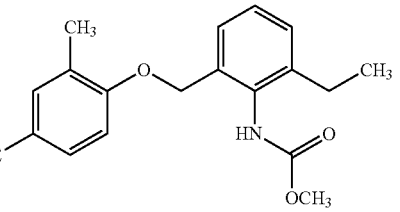
(HA1025)
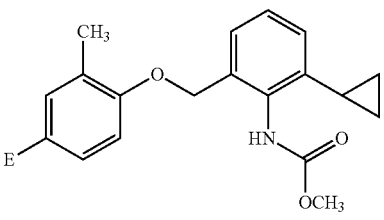

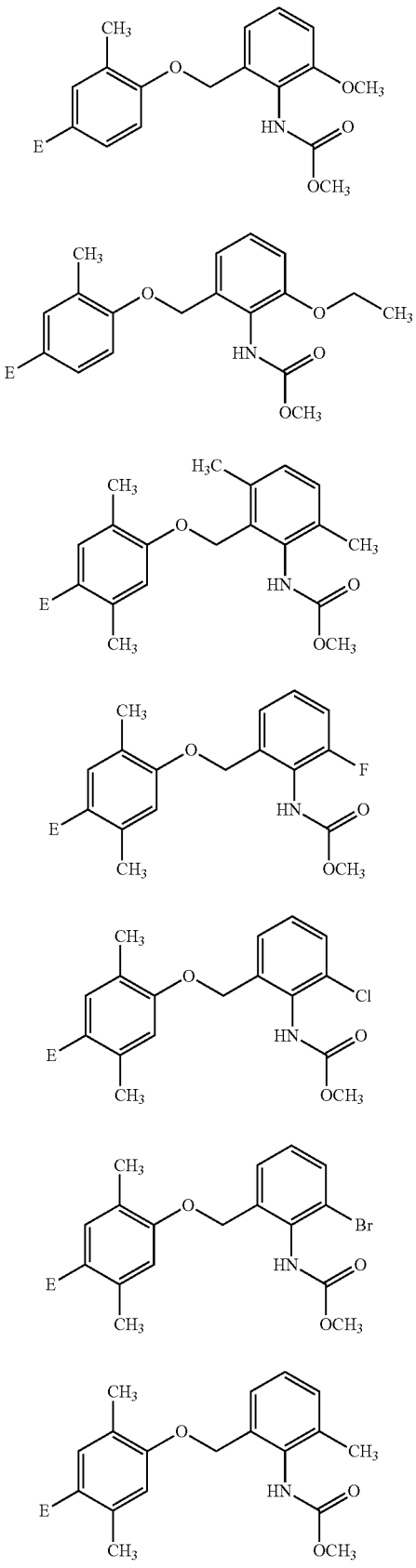
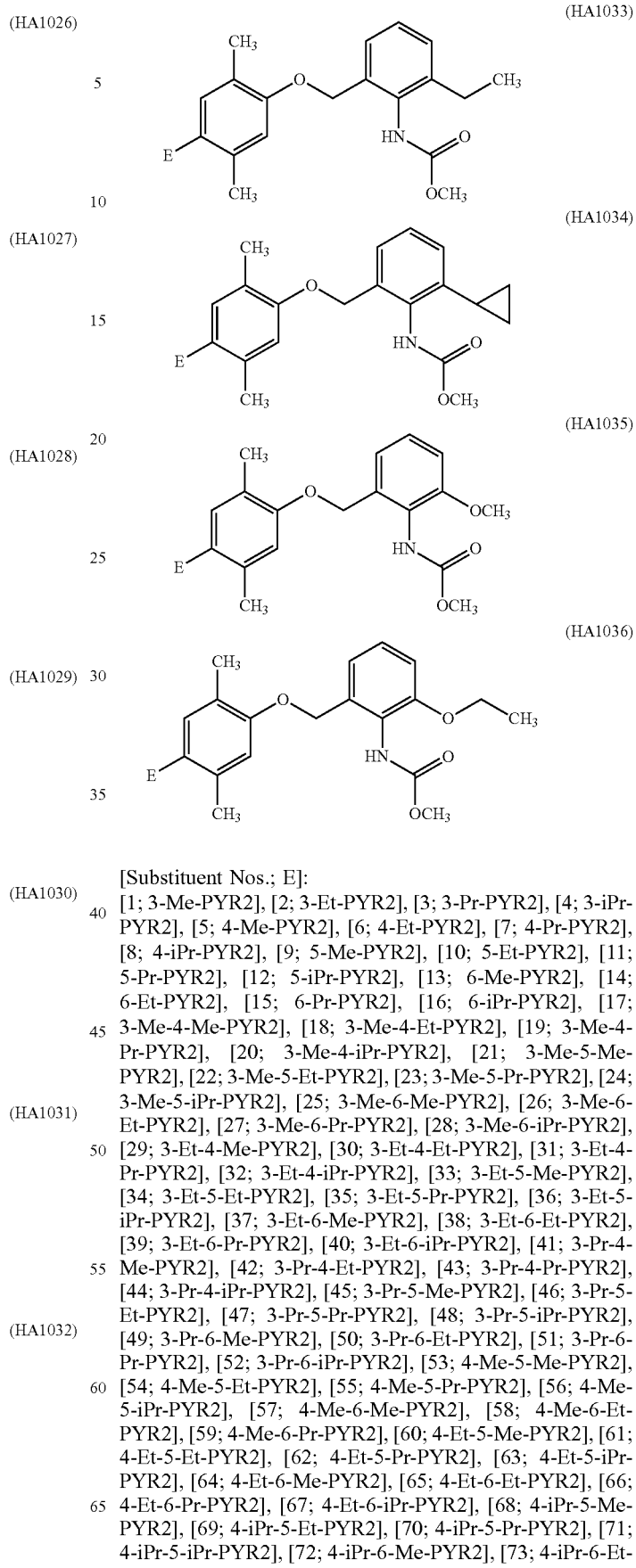

[Substituent Nos.; E]:
[1; 3-Me-PYR2], [2; 3-Et-PYR2], [3; 3-Pr-PYR2], [4; 3-iPr-PYR2], [5; 4-Me-PYR2], [6; 4-Et-PYR2], [7; 4-Pr-PYR2], [8; 4-iPr-PYR2], [9; 5-Me-PYR2], [10; 5-Et-PYR2], [11; 5-Pr-PYR2], [12; 5-iPr-PYR2], [13; 6-Me-PYR2], [14; 6-Et-PYR2], [15; 6-Pr-PYR2], [16; 6-iPr-PYR2], [17; 3-Me-4-Me-PYR2], [18; 3-Me-4-Et-PYR2], [19; 3-Me-4-Pr-PYR2], [20; 3-Me-4-iPr-PYR2], [21; 3-Me-5-Me-PYR2], [22; 3-Me-5-Et-PYR2], [23; 3-Me-5-Pr-PYR2], [24; 3-Me-5-iPr-PYR2], [25; 3-Me-6-Me-PYR2], [26; 3-Me-6-Et-PYR2], [27; 3-Me-6-Pr-PYR2], [28; 3-Me-6-iPr-PYR2], [29; 3-Et-4-Me-PYR2], [30; 3-Et-4-Et-PYR2], [31; 3-Et-4-Pr-PYR2], [32; 3-Et-4-iPr-PYR2], [33; 3-Et-5-Me-PYR2], [34; 3-Et-5-Et-PYR2], [35; 3-Et-5-Pr-PYR2], [36; 3-Et-5-iPr-PYR2], [37; 3-Et-6-Me-PYR2], [38; 3-Et-6-Et-PYR2], [39; 3-Et-6-Pr-PYR2], [40; 3-Et-6-iPr-PYR2], [41; 3-Pr-4-Me-PYR2], [42; 3-Pr-4-Et-PYR2], [43; 3-Pr-4-Pr-PYR2], [44; 3-Pr-4-iPr-PYR2], [45; 3-Pr-5-Me-PYR2], [46; 3-Pr-5-Et-PYR2], [47; 3-Pr-5-Pr-PYR2], [48; 3-Pr-5-iPr-PYR2], [49; 3-Pr-6-Me-PYR2], [50; 3-Pr-6-Et-PYR2], [51; 3-Pr-6-Pr-PYR2], [52; 3-Pr-6-iPr-PYR2], [53; 4-Me-5-Me-PYR2], [54; 4-Me-5-Et-PYR2], [55; 4-Me-5-Pr-PYR2], [56; 4-Me-5-iPr-PYR2], [57; 4-Me-6-Me-PYR2], [58; 4-Me-6-Et-PYR2], [59; 4-Me-6-Pr-PYR2], [60; 4-Et-5-Me-PYR2], [61; 4-Et-5-Et-PYR2], [62; 4-Et-5-Pr-PYR2], [63; 4-Et-5-iPr-PYR2], [64; 4-Et-6-Me-PYR2], [65; 4-Et-6-Et-PYR2], [66; 4-Et-6-Pr-PYR2], [67; 4-Et-6-iPr-PYR2], [68; 4-iPr-5-Me-PYR2], [69; 4-iPr-5-Et-PYR2], [70; 4-iPr-5-Pr-PYR2], [71; 4-iPr-5-iPr-PYR2], [72; 4-iPr-6-Me-PYR2], [73; 4-iPr-6-Et- PYR2], [74; 4-iPr-6-Pr-PYR2], [75; 4-iPr-6-iPr-PYR2], [76; 5-Me-6-Me-PYR2], [77; 5-Me-6-Et-PYR2], [78; 5-Me-6-Pr-PYR2], [79; 5-Me-6-iPr-PYR2], [80; 5-Et-6-Me-PYR2], [81; 5-Et-6-Et-PYR2], [82; 5-Et-6-Pr-PYR2], [83; 5-Et-6-iPr-PYR2], [84; 5-Pr-6-Me-PYR2], [85; 5-Pr-6-Et-PYR2], [86; 5-Pr-6-Pr-PYR2], [87; 5-Pr-6-iPr-PYR2], [88; 5-iPr-6-Me-PYR2], [89; 5-iPr-6-Et-PYR2], [90; 5-iPr-6-Pr-PYR2], [91; 5-iPr-6-iPr-PYR2], [92; 3-Me-4-Me-5-Me-PYR2], [93; 3-Et-4-Me-5-Me-PYR2], [94; 3-Pr-4-Me-5-Me-PYR2], [95; 3-iPr-4-Me-5-Me-PYR2], [96; 3-Me-4-Me-6-Me-PYR2], [97; 3-Et-4-Me-6-Me-PYR2], [98; 3-Pr-4-Me-6-Me-PYR2], [99; 3-iPr-4-Me-6-Me-PYR2], [100; 3-Me-5-Me-6-Me-PYR2], [101; 3-Et-5-Me-6-Me-PYR2], [102; 3-Pr-5-Me-6-Me-PYR2], [103; 3-Me-4-Et-5-Me-PYR2], [104; 3-Me-4-Pr-5-Me-PYR2], [105; 3-Me-4-iPr-5-Me-PYR2], [106; 4-Me-5-Me-6-Me-PYR2], [107; 4-Et-5-Me-6-Me-PYR2], [108; 4-Pr-5-Me-6-Me-PYR2], [109; 4-iPr-5-Me-6-Me-PYR2], [110; 4-Me-5-Et-6-Me-PYR2], [111; 4-Me-5-Pr-6-Me-PYR2], [112; 4-Me-5-iPr-6-Me-PYR2], [113; 3-Me-4-Me-5-Et-PYR2], [114; 3-Me-4-Me-5-Pr-PYR2], [115; 3-Me-4-Me-5-iPr-PYR2], [116; 4-Me-5-Me-6-Et-PYR2], [117; 4-Me-5-Me-6-Pr-PYR2], [118; 4-Me-5-Me-6-iPr-PYR2], [119; 3-Me-4-Me-6-Et-PYR2], [120; 3-Me-4-Me-6-Pr-PYR2], [121; 3-Me-4-Me-6-iPr-PYR2], [122; 3-Me-5-Et-6-Me-PYR2], [123; 3-Me-5-Pr-6-Me-PYR2], [124; 3-Me-5-iPr-6-Me-PYR2], [125; 3-Me-5-Me-6-Et-PYR2], [126; 3-Me-5-Me-6-Pr-PYR2], [127; 3-Me-5-Me-6-iPr-PYR2], [128; 3-Me-4-Me-5-Me-6-Me-PYR2].

For example, in the compound represented by formula HA1001, HA1001-46 is the compound represented by the following formula:

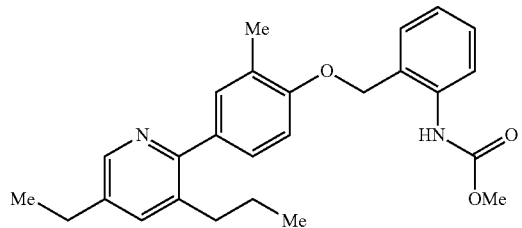

(HA1001-46)

wherein, substituent number is 46.

Formulation Examples are shown below. In the following Formulation Examples, part means part by weight.

Formulation Example 1

Fifty parts (50 parts) of any one of Compounds HA1001-1 to HA1036-128, 3 parts of calcium lignin sulfonate, 2 parts of magnesium lauryl sulfate, and 45 parts of synthetic hydrous silicon oxide are thoroughly ground and mixed to give a formulation.

Formulation Example 2

Twenty parts (20 parts) of any one of Compounds HA1001-1 to HA1036-128 and 1.5 parts of sorbitan trioleate are mixed with 28.5 parts of an aqueous solution containing 2 parts of polyvinyl alcohol; and the mixture is finely ground by a wet grinding method. Then, to the mixture, 40 parts of an aqueous solution containing 0.05 part of xanthan gum and 0.1 part of aluminum magnesium silicate is added, and 10 parts of propylene glycol is further added, followed by stirring and mixing to give a formulation.

Formulation Example 3

Two parts (2 parts) of any one of Compounds HA1001-1 to HA1036-128, 88 parts of kaolin clay, and 10 parts of talc are thoroughly ground and mixed to give a formulation.

Formulation Example 4

Five parts (5 parts) of any one of Compounds HA1001-1 to HA1036-128, 14 parts of polyoxyethylene styrylphenyl ether, 6 parts of calcium dodecylbenzenesulfonate, and 75 parts of xylene are thoroughly ground and mixed to give a formulation.

Formulation Example 5

Two parts (2 parts) of any one of Compounds HA1001-1 to HA1036-128, 1 part of synthetic hydrous silicon oxide, 2 parts of calcium lignin sulfonate, 30 parts of bentonite, and 65 parts of kaolin clay are thoroughly ground and mixed, followed by addition of water to the mixture; and the mixture is thoroughly kneaded and further granulated and dried to give a formulation.

Formulation Example 6

Twenty parts (20 parts) of any one of Compounds HA1001-1 to HA1036-128, 35 parts of a mixture of white carbon and ammonium polyoxyethylene alkyl ether sulfate (weight ratio 1:1), and 45 parts of water are mixed and finely ground by a wet grinding method to give a formulation.

Hereinafter, Test Examples are shown.

Test Example 1

Plastic pots each were filled with soil, and barley (cultivar: Mikamo-Golden) was sowed and grown in a greenhouse for 7 days. To the formulated present Compound 1, 2, 3 or 5 according to Formulation Example 6, water was added so as to adjust the water dilution to a predetermined concentration (500 ppm), and the adjusted dilution was sprayed over stems and leaves of the barley so that the liquid sufficiently adhered to surfaces of the leaves of the barley. After being sprayed, the barley was air-dried. After 2 days, an aqueous suspension containing spores of barley net blotch fungus (*Pyrenophora teres*) was sprayed to inoculate the spores. After completion of the inoculation, the barley was left to stand for 3 days in a greenhouse at 23° C. in the daytime and 20° C. at night under high humidity condition, and was cultivated in a greenhouse for 7 days; and then the area of the lesion was investigated. As a result, the area of the lesion on the barley treated with the present Compound 1, 2, 3 or 5 were 30% or less than those on untreated barley.

Test Example 2

Plastic pots each were filled with soil, and wheat (cultivar: Shirogane) was sowed and grown in a greenhouse for 9 days. To the formulated present Compound 1, 2, 3, 4 or 5 according to Formulation Example 6, water was added so as to adjust the water dilution to a predetermined concentration (200 ppm), and the adjusted dilution was sprayed over stems and leaves of the barley so that the liquid sufficiently adhered to surfaces of the leaves of the wheat. After being sprayed, the wheat was air-dried so as to dry the leaves. After the wheat was cultivated at 20° C. for 5 days under illumination, and then inoculated by sprinkling with spores of wheat rust fungus (*Puccinia recondita*). After the inoculation, the wheat was left to stand at 23° C. for one day under dark and high humidity condition, and cultivated under illumination at 20° C. for 8 days, and then the area of the lesion was investigated. As a result, it was found that the area of the lesion on the wheat treated with the present Compound 1, 2, 3, 4 or 5 were 30% or less than those on untreated wheat.

Meanwhile, in the same test using methyl N-(2-{[4-(pyridine-2-yl)phenoxy)methyl}phenyl)carbamate in place of the present Compounds, the result was 70% or more than those on the untreated plant.

Test Example 3

Plastic pots each were filled with soil, and rice (cultivar: Nipponbare) was sowed and grown in a greenhouse for 20 days. To the formulated present Compound 2 or 3 according to Formulation Example 6, water was added so as to adjust the water dilution to a predetermined concentration (500 ppm), and the adjusted dilution was sprayed over stems and leaves of the rice so that the liquid sufficiently adhered to surfaces of the leaves of the rice. After being sprayed, the rice was air-dried; and the rice subjected to the spray treatment was placed in contact with rice seedling (cultivar: Nipponbare) infected by rice blast fungus (*Magnaporthe grisea*), and these two plants were left to stand for 6 days at 24° C. in the daytime and 20° C. at night under high humidity condition; and then the area of the lesion of the rice was investigated. As a result, the lesion areas on the rice treated with the present compound 2 or 3 were 30% or less than those on the untreated plant.

Test Example 4

Plastic pots each were filled with soil, and kidney bean (cultivar: Nagauzura Saito) and was sowed and grown in a greenhouse for 8 days. To the formulated present Compound 1, 2, 3 or 5 according to Formulation Example 6, water was added so as to adjust the water dilution to a predetermined concentration (500 ppm), and the adjusted dilution was sprayed over stems and leaves of the kidney bean so that the liquid sufficiently adhered to surfaces of the leaves of the kidney bean. After being sprayed, the kidney bean was air-dried, and a PDA medium containing hyphae of the kidney bean stem rot fungus (*Sclerotinia sclerotiorum*) was placed on the leaves of the kidney bean. After the inoculation, all of the kidney beans were left to stand under high humidity condition only at night. Four days after the inoculation, the area of the lesion was investigated. As a result, the area of the lesion on the kidney bean treated with the present compound 1, 2, 3 or 5 was 30% or less than those on untreated kidney bean.

Test Example 5

Plastic pots each were filled with soil, and wheat (cultivar: Apogee) was sowed and grown in a greenhouse for 10 days. To the formulated present Compound 1, 2, 3, 4 or 5 according to Formulation Example 6, water was added so as to adjust the water dilution to a predetermined concentration (200 ppm), and the adjusted dilution was sprayed over stems and leaves of the wheat so that the liquid sufficiently adhered to surfaces of the leaves of the wheat. After being sprayed, the wheat was air-dried. After 4 days, an aqueous suspension containing spores of wheat speckled leaf blotch fungus (*Septoria tritici*) was sprayed to inoculate the spores. After completion of the inoculation, the wheat was left to stand at 18° C. under high humidity condition for 3 days and left to stand under illumination for 14 to 18 days, and then the area of the lesion was investigated. As a result, the area of the lesion on the wheat treated with the present compound 1, 2, 3, 4 or 5 were 30% or less than those on untreated wheat.

Test Example 6

Plastic pots each were filled with soil, and cucumber (cultivar: Sagami Hanjiro) was sowed and grown in a greenhouse for 12 days. To the formulated present Compound 1, 2, 3 or 5 according to Formulation Example 6, water was added so as to adjust the water dilution to a predetermined concentration (500 ppm), and the adjusted dilution was sprayed over stems and leaves of the cucumber so that the liquid sufficiently adhered to surfaces of the leaves of the cucumber. After being sprayed, the cucumber was air-dried, and then inoculated by being sprinkled with spores of cucumber powdery mildew fungus (*Sphaerotheca fuliginea*, a QoI-resistant strain in which, among the genes encoding cytochrome b, the amino acid residue at position 143 of cytochrome b was mutated from glycine to alanine). After the inoculation, the cucumber was cultivated in a greenhouse at 24° C. in the daytime and 20° C. at night for 8 days, and then the area of the lesion was investigated. As a result, the area of the lesion on the cucumber treated with the present compound 1, 2, 3 or 5 were 30% or less than those on untreated cucumber.

INDUSTRIAL APPLICABILITY

The carbamate compounds of the present invention are effective at controlling plant diseases, and are useful as active ingredients of plant disease controlling agents.

The invention claimed is:
1. A carbamate compound represented by the formula (I):

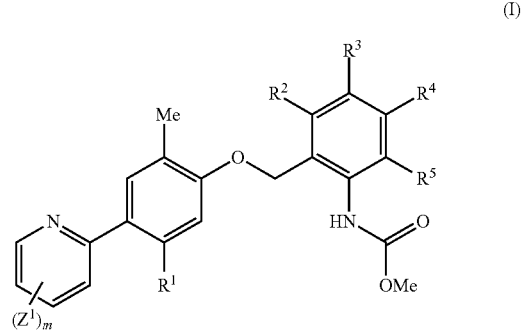

wherein,
R$^1$ represents a hydrogen atom or a C1-C3 alkyl group;
R$^2$ represents a methyl group;
R$^3$, R$^4$ and R$^5$ each independently represents a hydrogen atom;
Z$^1$ represents a C1-C3 alkyl group; and
m represents any one of integers from 1 to 4.
2. A carbamate compound according to claim 1, wherein R$^1$ is a hydrogen atom, Z$^1$ is a methyl or ethyl group, and m is 1.

3. A carbamate compound according to claim 1, wherein $R^1$ is a hydrogen atom, $Z^1$ is a methyl group, and m is 1.

4. A plant disease controlling agent, which comprises a carbamate compound represented by formula (I):

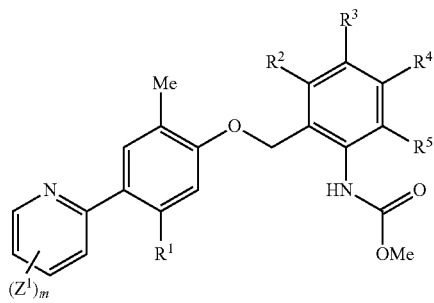

wherein,
- $R^1$ represents a hydrogen atom or a C1-C3 alkyl group;
- $R^2$ represents a methyl group;
- $R^3$, $R^4$ and $R^5$ each independently represents a hydrogen atom;
- $Z^1$ represents a C1-C3 alkyl group; and
- m represents any one of integers from 1 to 4, as an active ingredient.

5. A method for controlling plant diseases by treating plants or soil for cultivating plants with an effective amount of a carbamate compound represented by formula (I):

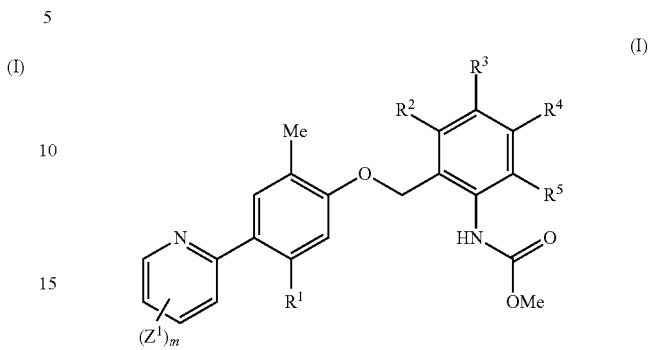

wherein,
- $R^1$ represents a hydrogen atom or a C1-C3 alkyl group;
- $R^2$ represents a methyl group;
- $R^3$, $R^4$ and $R^5$ each independently represents a hydrogen atom;
- $Z^1$ represents a C1-C3 alkyl group; and
- m represents any one of integers from 1 to 4.

* * * * *